United States Patent [19]

Kinnett

[11] Patent Number: 4,550,450
[45] Date of Patent: Nov. 5, 1985

[54] TOTAL SHOULDER PROSTHESIS SYSTEM

[76] Inventor: James G. Kinnett, 5534 St. Charles Ave., New Orleans, La. 70115

[21] Appl. No.: 634,482

[22] Filed: Jul. 24, 1984

[51] Int. Cl.⁴ .............................................. A61F 1/24
[52] U.S. Cl. ................................................... 623/18
[58] Field of Search .......................... 3/1.91; 128/92 C

[56] References Cited

U.S. PATENT DOCUMENTS 3,694,820  10/1972  Scales et al. ........................... 3/1.91
4,042,980   8/1977  Swanson et al. ................... 128/92 C Primary Examiner—Richard J. Apley
Assistant Examiner—James Prizant
Attorney, Agent, or Firm—Mason, Fenwick & Lawrence

[57] ABSTRACT

A total shoulder replacement arthroplasty system which encompasses replacement of the articular surface of the humerus and adjacent glenoid articular surface with a humeral component having a convex surface and a shallow trapezoidal fixation keel to avoid violation of the medullary cavity by the prosthesis and with a concave overmounted glenoid component having a similar keel. The inferior aspect of the acromion is resurfaced with an acromial component for replacement of the acromial clavicular joint, providing mechanical advantage of a fulcrum for abduction and forward flexion of the humerus, and preventing superior migration of the humerus.

23 Claims, 8 Drawing Figures

TOTAL SHOULDER PROSTHESIS SYSTEM

PRIOR RELATED APPLICATIONS

The prothesis components of this application embody the designs of my prior applications Ser. No. 570,253 filed Jan. 12, 1984, Ser. No. 575,930 filed Jan. 31, 1984 and Ser. No. 576,131 filed Feb. 1, 1984.

BACKGROUND AND OBJECTS OF THE INVENTION

The present invention relates in general to joint prothesis systems for joints of the human body, and more particularly to a total shoulder replacement arthroplasty for replacement of confronting surfaces of the shoulder joint.

The shoulder joint, the largest joint in the upper extremity, functions as the fulcrum for all functional activities of the upper extremity, and also affords the greatest range of motion and planes of motion of any joint in the body. These unique characteristics of relatively high force transmission as well as the large range of motion afforded by the unique anatomical structure of this joint, impart certain difficult considerations in total shoulder prosthetic design. The design must allow for the shoulder to be the foundation joint for the upper extremity with its large range of motion as well as for the limited osseous framework available for fixation of the device. Additional considerations include the proximity of neural and vascular anatomic structures, the usual difficult surgical approach to the shoulder secondary to major muscular structures, and the relationship of the acromiom to the gleno-humeral articulation.

Much prior prosthetic replacement development has been directed at the hip and knee joints, the major weight bearing joints of the lower extremity. However, these joints have a much less complex and extensive range of motion and the anatomical considerations in these joints, especially the hip, are much less complicated than the shoulder. The surgical approach to the hip and the knee is generally considered less demanding than the surgical approaches to the shoulder joint.

Of the several surgial options available for the painful shoulder with limited or no motion, gleno-humeral replacement commonly accepted as total joint replacement for the shoulder has offered the best solution for problems of the entire shoulder joint to date. At present there are two basic categories of prosthesis available. These include constrained prosthesis and essentially unconstrained prosthesis. The major problems with the constrained prosthesis occur as in all constrained prosthesis, i.e., limited motion, mechanical failure, and loosening. In the unconstrained category the prosthesis usually available utilizes surface or flush glenoid components with fixation devices directed to the anatomical cancellous region of the scapulae. Fixation of the glenoid component has and continues to be considered a problem. Incomplete recovery of range of motion primarily in abduction and forward flexion has been encountered and appears to be related to overall prosthetic design. Violation of the medullary cavity of the humerous should be avoided, if possible. Another problem area in the present gleno-humeral replacement is proximal subluxation of the humerus with resulting humeral acromial impingement.

The shoulder is a complex articulation that involves the proximal humerus, the glenoid, the acromion, the clavicle and the scapulo-thoracic non-synovial articulation. The pathological process resulting in diseased and nonfunctional shoulders almost universally involve the articulation comprised of humerus, glenoid and acromion. Prior prosthetic designs with one exception, have not considered the acromial component.

Problems have been recognized in the presently available flush or surface mounted concave glenoid components in regard to dislocation of the humeral component and fixation. The flush mounted component offers a limited surface for attachment, thus necessarily limiting the surface area that may be provided for articulation with the humeral component. Recent design modifications to accommodate the acromial function would impart additional shear forces to the already tenuous glenoid component fixation and therefore contribute to the possibility of loosening. The surface mounted concave glenoid components now available offer no restriction to malposition referrable to retroversion or anteversion of the glenoid component.

Substantially all humeral component designs presently available utilize stemmed prosthesis. The experience with violation of the medullary cavity for placement of the stem and for fixation based on other joint prosthesis is well known. Violation of the medullary cavity increases blood loss and the amount of dissection required thereby increasing the likelihood of infection. An intramedullary stem significantly increases the surgical task, anesthesia time and blood loss should replacement of the humeral or stemmed prosthesis for any joint be necessary. The amount of methyl methacrylate and the surface exposed to the methacrylate is significantly increased with stem prosthesis thereby resulting in increased avascular or hypovascular tissue present in the wound which may be a contributing factor in late infection.

An object of the present invention, therefore, is the provision of a true total shoulder replacement arthroplasty system which encompasses replacement of the articular surface of the humerus with a convex surface replacement without a traditional stem and without violation of the medullary cavity by the prosthesis, and wherein the glenoid surface is replaced by a concave overmounted component, and the inferior aspect of the acromion is resurfaced with an acromial component for prevention of proximal subluxation.

A further object of the present invention is the provision of a shoulder replacement arthroplasty system as defined in the immediately preceding paragraph, wherein the acromial clavicular joint is replaced and mechanical advantage of a fulcrum is provided for abduction and forward flexion of the humerus.

Other objects, advantages, and capabilities of the present invention will become apparent from the following detailed description, taken in conjunction with the accompany drawings illustrating a preferred embodiment of the invention.

DETAILED DESCRIPTION OF A PREFERRED EMBODIMENT

Figure 1:
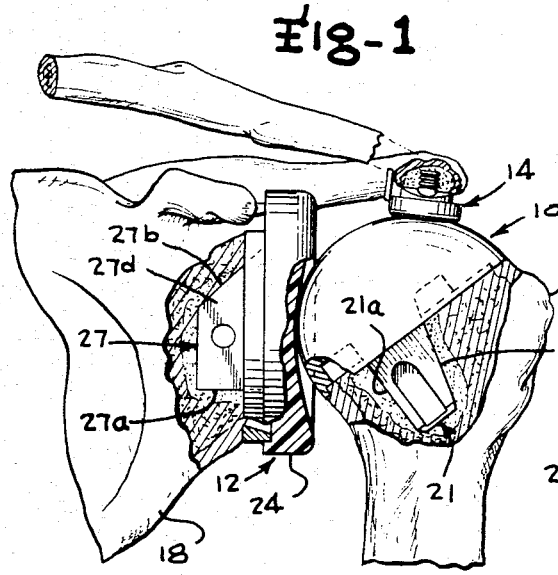
FIG. 1 is a fragmentary front elevational view of a shoulder joint with the total shoulder replacement prostheses of the present invention in place, and with parts broken away to reveal imbedded structure on the humeral, glenoid and acromial components.

Referring to the drawings, wherein like reference characters designate corresponding parts throughout the several figures, the total shoulders prosthesis system of the present invention comprises, as previously described, instead of the usual two prosthesis components for attachment to the scapula and humerus, a three component total shoulder replacement arthroplasty prosthesis system, comprising a humeral component 10, to be implanted with secure fixation on the proximal humerus portion, and a glenoid component 12 to be fixed on the adjacent surface of the scapula, the humeral component to coact with an acromial component 14 to be placed as a resurfacing portion of the inferior aspect of the acromion.

As best shown in FIG. 1, the humeral component 10 forms a proximal humerus head to replace the humeral head surface of the humerus 16, having a complex somewhat hemispherical surface confronting and engaging a concave surface portion of the glenoid component 12, which is fixed as later described, to the scapula, indicated by the reference character 18, to form a replacement surface for the surface portions of the scapula normally engaging the head of the humerous 16. The acromial component 14 is to replace the acromioclavicular articulation, in effect resurfacing the under surface of the acromion, after resection of a portion of the distal clavical.

Figure 2:
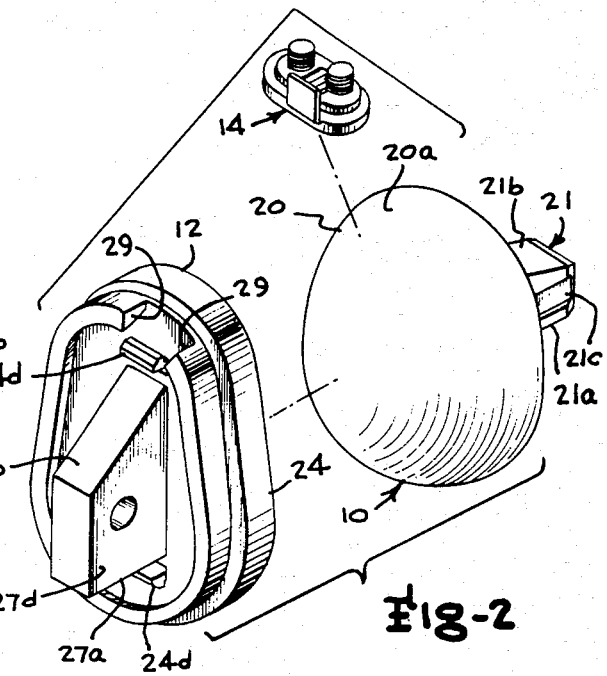
FIG. 2 is an exploded perspective view of the glenoid, humeral and acromial components.
Figure 5:
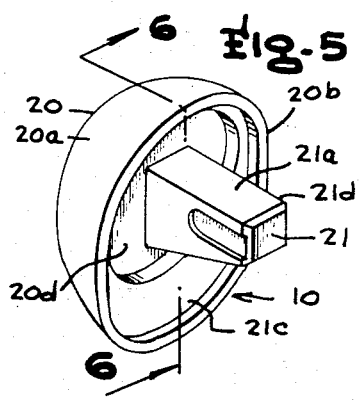
FIG. 5 is a rear perspective view of the humeral component viewed from the end opposite that shown in FIG. 2.
Figure 6:
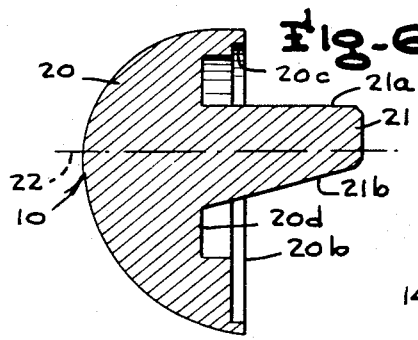
FIG. 6 is a vertical section view through the humeral component taken along the line 6—6 of FIG. 5.
Figure 8:
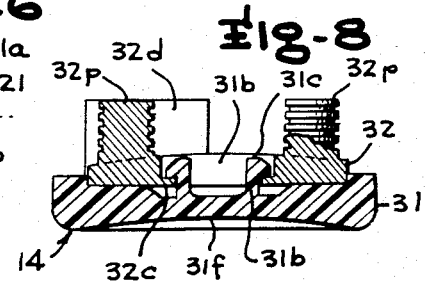
FIG. 8 is a vertical section view of the acromial component, taken along the line 8—8 of FIG. 7.

The humeral component 10, as shown in greater detail in FIGS. 2, 5 and 6, is a convex chrome cobalt molyibium pseudo-hemisphere made up in the coronal plane of two arcs. The convex pseudo-hemispherical main body portion 20 thereof has the psuedo-hemispherical surface 20a formed such that the radius of the superior arc is 44 mm, the radius of the medial arc is 40 mm, and the radius of the arc in the sagittal plane at the midpoint is 44 mm. The rear face 20b of the humeral component 10 is recessed to provide a larger diameter well portion 20c of generally ovaloid configuration, joining a deeper smaller diameter ovaloid well 20d, from the root or base wall of which a trapezoidal fixation keel 21 extends rearwardly, projecting from the non-articulating surface or rear face 20b of the humeral component 10. The fixation keel 21 has a first end surface 21a which parallels the center axis indicated in broken lines and designated by reference character 22 of the humeral component 10 and an opposite second end surface 21b which is inclined in rearwardly converging relation to the opposite end surface 21a forming the trapezoidal cross sectional configuration best observed in FIG. 6, while the side surfaces 21c and 21d of trapezoidal fixation keel parallel each other and also parallel the center axis 22 in planes perpendicular to the plane of the first end surface 21a. This differs from previous know surface replacements for the proximal humerus which encompass a single radius arc and around fixation peg which provides significantly less resistance to torque.

Figure 3:
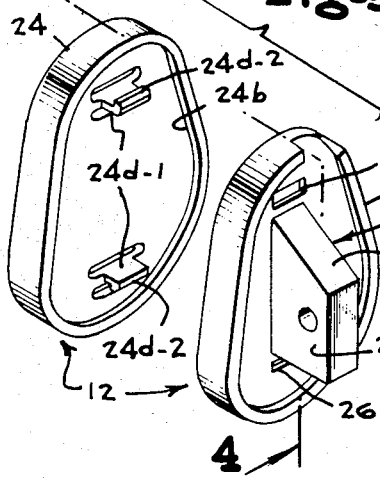
FIG. 3 is an exploded perspective view of the base and contact surface members of the glenoid component.
Figure 4:
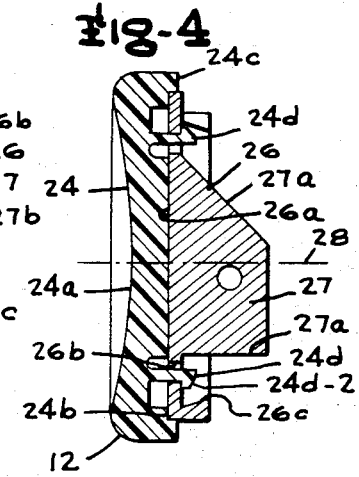
FIG. 4 is a vertical section view through the glenoid component taken along the line 4—4 of FIG. 3.
Figure 7:
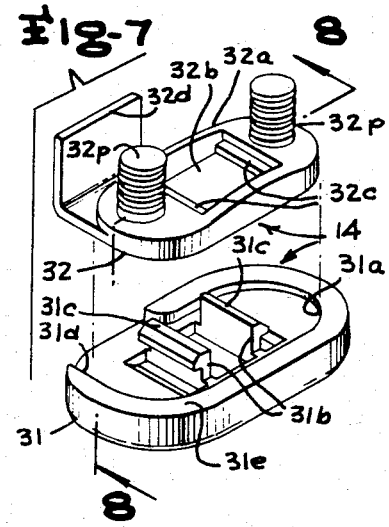
FIG. 7 is an exploded perspective view of the acromial component, showing the cover surface component exploded from the base component.

The glenoid component 12, best illustrated in FIGS. 2, 3 and 4, is a two part assembly comprising, in the preferred embodiment, a high molecular weight polyethylene concave articular surfaced component 24 and a titanium base tray component 26. The polyethylene component 24 is shaped to provide a concave articular surface 24a measuring 2 cm in the AP plane and 2.5 cm in the sagittal plane having rounded corners. It is shaped to provide a recess or well 24b and its rearwardly facing surface 24c has the shape as shown in FIG. 3 providing a configuration to receive in tightly nested relation the confronting face 26a of the base component 26. The polyethylene component 24 also includes a pair of rearwardly projecting hook flange formations 24d having slightly flexible rib like body portions 24d-1 and truncated triangular shoulder-forming heads 24d-2 to extend through and be captured by interlocking slots 26b in the base portion 26. The titanium base component 26 is 2.5 mm wide with a recess located in the anterior-superior aspect of the base member 26 to correspond with the normal anatomical position of the coricoid. A trapezoidal shaped fixation keel 27 is provided on the base member 26 projecting rearwardly for fixation into the cancellous component of the scapular neck. The fixation keel 27 for the glenoid component 12, like the fixation keel 21 of the humeral component 10, has a first end surface 27a paralleling the center axis of the glenoid component, indicated by the broken lines and reference character 28, and inclined opposite second surface 27b converging rearwardly relative to the surface 27a and parallel side surfaces 27c and 27d extending perpendicular to the surface 27a and also lying in planes paralleling the center axis 28. The base portion 26 provides additional surface area for fixation as well as additional stability for sheer forces. The fixation keel 27 provides increased mechanical advantages against torque and provides increased surface area for fixation. The base member 26 is provided with a coricoid notch 29, best shown in FIGS. 2 and 3, to insure appropriate anatomic placement of the glenoid component 12 without respect for the articular surface of the natural glenoid which may be destroyed in the disease process. The increased area and mechanical advantage provided by the glenoid base portion 26 and the lack of any superior restraining aspect of the glenoid component 12 allows for more substantial fixation and reduced forces. The resulting stabilitiy allows for an increased surface area for articulating with the humeral component to prevent dislocation.

The third and crucial component in my system, which to my knowledge has not essentially been offered in any prior shoulder prosthesis design, is the acromial component 14. The acromial component 14 consists of a 1 mm titanium backed high molecular weight polyethylene component, comprising the generally oval shaped polyethylene facing member 31 and the titanium backing member 32. The polyethylene backing member 32 is approximately 3 mm thick and has a rearwardly facing recess 31a to receive the main body portion 32a of the backing member and a pair of rearwardly projecting and oppositely extending catch hook flange formations 31b each having a truncated triangular shoulder-forming head 31c, to extend through the substantially rectangular opening 32b and interlock with the shoulder formations 32c bounding to opposite edges of the opening 32b. A right angular flange-like extension 32d extends laterally from one end portion of the backing member 32 through a relieved cut out or opening 31d in the lip portion 31e to facilitate location and stabilization of the acromial component 14. The backing member 32 also has a pair of fixation pegs 32p of alternating annular ribs and grooves, as shown, along their surface, projecting from the backing member 32.

The backing member 32 of the acromial component 14 has a right angle perpendicular extension arm structure, referred to previously as the right angular flange formation 32d, of titanium to correspond to the acromial surface of the acromial clavicular joint. A portion of the distal clavical is resected at surgical placement. The acromial component 14 is essentially of rectangular configuration having rounded end portions producing a somewhat oval shape measuring about 2 cm by 2.5 cm and having a concave abutment surface, indicated at 31f toward the articular surface of the humerus with a radius arc of about 44 mm. The function of this component is to replace the acromio-clavicular articulation, re-surface the degenerative under surface of the acromion, provide a physiologic replacement for the subacromial bursae, prevent superior subluxation of the humerus, and provide a buffer for protection of the rotator cuff which passes between the prosthetic or natural humerus and the prosthetic or natural acromion.

The articulated components 10, 12 and 14 provide surface replacement for the humerus, glenoid and the acromion. The unconstrained design of the prosthesis facilities increased range of motion as well as reducing the forces across the fixation interface of the components. The major pain producing surfaces in the shoulder, namely the glenoid, the humerus, the acromio-clavicular articulation and the inferior surface of the acromion are thus eliminated. The prosthesis has the increased mechanical advantage of having an increased radius of the superior arc of the humeral component 10 for articulation with the relatively flat acromial component 14, a smaller radius of the arc medially for articulation with the glenoid component 12 to increase the internal and external rotation range. The acromial component 14 eliminates the proximal or superior subluxation of the humeral component 10 and in addition, by providing a fulcrum for the humerus, increases the mechanical advantage in abduction and forward flexion. The increased surface area for articulation of the glenoid component 12 prevents or aids in prevention of dislocation at the gleno-humeral articulation. Enlarging the surface area of the glenoid component 12 is made possible by eliminating the increased shear forces resulting from the superior block on the glenoid component to prevent proximal migration of the humerus and the increased fixation provided by the base member 26. The coricoid notch 29 provided in the base member 26 of the glenoid component 12 significantly aids in obtaining the proper position in relation to anteversion and retroversion of the glenoid component 12.

The procedure for installation of this total shoulder prosthesis system is substantially as follows:

After adequate preoperative medication, the patient is brought to the operating room, placed on the operating table, where after suitable general anesthesia has been obtained, the patient is positioned in a beach chair fashion with a roll under the scapula. The involved extremity is then prepped with antimicrobial scrub and antimicrobial solution in the usual sterile fashion and draped free using stockenett and paper drapes.

The shoulder is approached anteriorly through a deltapectoral incision with the incision commencing at the coracoid and extending distally along the anterior surface of the humerus to the midportion of the deltoid. The dissection is carried sharply down. Hemostasis is obtained where indicated using electrocautery or suture ligatures. The deltapectoral interval is identified. The cephalic vein may be retracted medially or laterally depending upon the contributing branches. After mobilizing the deltoid and the pectoralis, the clavipectoral fascia is identified and sharply incised. The conjoined tendon would be sharply incised for approximately 50% of its origin from the coracoid to allow easy visualization. Thereafter, the subscapularis tendon inserting on the lesser tuberosity is taken down using an electrosurgical unit, the inferior identifying portion being the vena comatantis of the medial humeral circumflex artery. The anterior capsule of the shoulder is then identified and an anterior capuslotomy is carried out. A complete dissection of the origin of the glenoid labrum is then effected and carefully removed so that the entire surface of the glenoid is identified. Thereafter, the interval between the greater tuberosity and the lesser tuberosity at the region of the intertubercular sulcus is identified and a hole is established through the articulating surface into the medullary cavity of the humerus using a Cobb type gouge. The hole is enlarged to receive the intermedullary portion of the humeral cutting device which is inserted. Thereafter, using an oscillating saw, a proximal-humeral osteotomy is effected removing only the articular surface of the proximal humerus. The cutting guide is then removed, a template is placed on the resected proximal portion of the humerus and a centering pin driven through the proximal humerus into the lateral humeral cortex. The power reamer is fitted over the guide pin and the proximal humerus reamed. Visualization would then be effected by using a modified Bankart T-handled retractor; the glenoid is easily visualized; the glenoid template is placed into position; a blow is struck on the template to allow a marking incision to be made on the glenoid; the template is then removed; and using a high speed Hull-type burr the portion of the glenoid face to be resected to allow placement of the glenoid component 12 is effect. The articular surface is removed using the Hull burr and the area for the glenoid fixation keel 27 would be cleared of medullary bone using a Hull burr. Curettes may be used to establish fixation holes into the coracoid and into the lateral border of the scapula at this time.

Attention is then directed to the acromo-clavicular articulation and approximately 1 cm of the distal clavical is resected using the handle of the acromial template as a guide for the resection. Thereafter, the acromial template is placed on the acromion, the area for the fixation pegs 32p of the acromial component 14 is marked with methylene blue and the surface of the underneath aspect of the acromion would be marked for later removal with a Hull burr. Thereafter, the template is removed and, again using a high speed Hull-type burr, the cortical underneath surface of the acromion is removed to cancellous bone. Drill holes would be established to accept the fixation pegs 32p of the backing member 32 of the acromial component 14.

At this time, the entire wound is irrigated and hemostasis is obtained. All prepared bone surfaces are packed to achieve hemostasis for application of methyl methacrylate. Then, in a sequential manner, methyl methacrylate is prepared in the usual sterile fashion, and after obtaining suitable consistency small portions are placed on the underneath surface of the previously prepared acromion and the acromial component 14 of the appropriate size is placed on the underneath surface of the acromion. After curing of the methyl methacrylate, attention would be directed to the glenoid component 12 where, again after adequte pack and preparation of the bone surface, methyl methacrylate is prepared in the usual sterile fashion and applied to the glenoid component 12, then using the glenoid inserting instrument the appropriate size glenoid component 12 is inserted into the glenoid and impacted or, to use the mechanical term, coined into position and held with constant pressure until the methyl methacrylate cured. All excess methyl methacrylate would be removed from the surrounding bone surface on each component prior to curing. After the methyl methacrylate had cured on the glenoid component 12, attention would be directed to the humerus where again methyl methacrylate would be prepared in the usual sterile fashion. After obtaining suitable consistency an adequate portion is placed onto the proximal humerus, the humeral component 10 is placed into position, coined into position and held with constant pressure until the methyl methacrylate cured. All excess methyl methacrylate is removed prior to curing.

The only additional step of the operative procedure would be that following usual surgical technique, the medullary cavity of the humerus would be plugged with a cancellus bone graft obtained from the humeral head prior to introduction of methyl methacrylate. Thereafter, inspection of the components is completed; a capsulorrhaphy is carried out at the anterior shoulder capsulotomy; the subscapularis tendon is repaired in a standard surgical fashion; and the remaining closure of the wound follows standard techniques. Drains are used in the wound.

I claim:

1. A total shoulder replacement prosthesis system for replacement of the articular surface portions of the humerus and glenoid and resurfacing of a portion of the acromion, comprising a humeral prosthesis component having a convex main body portion shaped to provide a complex generally hemispherical head formation defining a generally ovaloid rear face disposed generally perpendicular to a center axis of the component and a convex pseudo-hemispherical articulating front surface extending forwardly from the rear face, the humeral component having a fixation keel projecting integrally from the body portion from the mid region of said rear face for a distance substantially not greater than the maximum depth dimension of the pseudo-hemispherical head formation to be implanted on the proximal humerus portion of a shoulder and having a non-round cross-sectional configuration, a glenoid component formed of a two-part assembly of a rigid member and an articular member of plastic material shaped to provide a shallow concave articular surface to articulate with the front surface of the humeral component and having rounded corners bounding the concave surface and a rearwardly facing well and deflectable shouldered catch projections to nestingly receive a flat confronting face of the articular component in said well and interlock with said catch projections, said base member of the glenoid component having a rearwardly projecting integral fixation keel of similar shape and depth of projection as the humeral component keel to be implanted on the scapular portion adjacent the humerus, and an acromial component to be fixed on a resurfaced portion of the inferior aspect of the acromion formed as a two piece assembly of a rigid backing member and a plastic generally oval shaped facing member having a shallow concave articular front face and a rear face secured against a confronting face of the backing member, interfitting catch formations projecting from one to the other of the acromial component members to interlock them together, and the backing member having fixation projection formation means to be implanted in the resurfaced acromion portion.

2. A shoulder replacement prosthesis system as defined in claim 1, wherein the fixation keel of said humeral component is of substantially trapezoidal configuration in side elevation.

3. A shoulder replacement prosthesis system as defined in claim 1, wherein the fixation keel of said humeral component is of substantially trapezoidal configuration in side elevation and has a pair of parallel planar sides.

4. A shoulder replacement prosthesis system as defined in claim 1, wherein the fixation keel of said humeral component is of substantially trapezoidal configuration in side elevation and has a pair of parallel planar sides and rearwardly converging top and bottom planar surfaces with one of the two latter surfaces extending perpendicular to the rear face of the humeral component.

5. A shoulder replacement prosthesis system as defined in claim 1, wherein the fixation keel of said glenoid component is of substantially trapezoidal configuration in side elevation.

6. A shoulder replacement prosthesis system as defined in claim 1, wherein the fixation keel of said glenoid component is of substantially trapezoidal configuration in side elevation and has a pair of parallel planar sides.

7. A shoulder replacement prosthesis system as defined in claim 1, wherein the fixation keel of said glenoid component is of substantially trapezoidal configuration in side elevation and has a pair of parallel planar sides and rearwardly converging top and bottom planar surfaces with one of the two latter surfaces extending perpendicular to the rear face of the humeral component.

8. A shoulder replacement prosthesis system as defined in claim 1, wherein said formation means of the acromial component are a pair of spaced apart substantially cylindrical peg formations having indentations along the cylindrical surface thereof.

9. A shoulder replacement prosthesis system as defined in claim 1, wherein said formation means of the acromial component are a pair of spaced apart substantially cylindrical peg formations having annular grooves at plural axially spaced positions along the cylindrical surface thereof.

10. A shoulder replacement prosthesis system as defined in claim 4, wherein said formation means of the acromial component area a pair of spaced apart substantially cylindrical peg formations having indentations along the cylindrical surface thereof.

11. A shoulder replacement prosthesis system as defined in claim 4, wherein said formation means of the acromial component are a pair of spaced apart substantially cylindrical peg formations having annular grooves at plural axially spaced positions along the cylindrical surface thereof.

12. A shoulder replacement prosthesis system as defined in claim 7, wherein said formation means of the acromial component are a pair of spaced apart substantially cylindrical peg formations having indentations along the cylindrical surface thereof.

13. A shoulder replacement prosthesis system as defined in claim 7, wherein said formation means of the acromial component are a pair of spaced apart substantially cylindrical peg formations having annular grooves at plural axially spaced positions along the cylindrical surface thereof.

14. A shoulder replacement prosthesis system as defined in claim 1, wherein the glenoid component articular member and the acromial component facing member are formed of high molecular weight polyethelene plastic, and their companion base member and backing member and said humeral component are formed of rigid metallic material.

15. A shoulder replacement prosthesis system as defined in claim 1, wherein the glenoid component articular member and the acromial component facing member are formed of high molecular weight polyethelene plastic, and their companion base member and backing member and said humeral component are formed of titanium.

16. A shoulder replacement prosthesis system as defined in claim 1, wherein the glenoid component articular member and the acromial component facing member are formed of high molecular weight polyethelene plastic, their companion base member and backing member are formed of titanium and said humeral compoent is formed of chrome cobalt molybdenum.

17. A shoulder replacement prosthesis system as defined in claim 4, wherein the glenoid component articular member and the acromial component facing member are formed of high molecular weight polyethelene plastic, and their companion base member and backing member and said humeral component are formed of rigid metallic material.

18. A shoulder replacement prosthesis system as defined in claim 4, wherein the glenoid component articular member and the acromial component facing member are formed of high molecular weight polyethelene plastic, and their companion base member and backing member and said humeral component are formed of titanium.

19. A shoulder replacement prosthesis system as defined in claim 4, wherein the glenoid component articular member and the acromial component facing member are formed of high molecular weight polyethelene plastic, their companion base member and backing member are formed of titanium and said humeral component is formed of chrome cobalt molybdenum.

20. A shoulder replacement prosthesis system as defined in claim 7, wherein the glenoid component articular member and the acromial component facing member are formed of high molecular weight polyethelene plastic, and their companion base member and backing member and said humeral component are formed of rigid metallic material.

21. A shoulder replacement prosthesis system as defined in claim 7, wherein the glenoid component tray member and the acromial component facing member are formed of high molecular weight polyethelene plastic, and their companion base member and backing member and said humeral component are formed of titanium.

22. A shoulder replacement prosthesis system as defined in claim 7, wherein the glenoid component tray member and the acromial component facing member are formed of high molecular weight polyethelene plastic, their companion base member and backing member are formed of titanium and said humeral component is formed of chrome cobalt molybdenum.

23. A shoulder replacement prosthesis system as defined in claim 8, wherein the glenoid component tray member and the acromial component facing member are formed of high molecular weight polyethelene plastic, and their companion base member and backing member and said humeral component are formed of rigid metallic material.

* * * * *